US006239141B1

(12) United States Patent
Allen et al.

(10) Patent No.: US 6,239,141 B1
(45) Date of Patent: May 29, 2001

(54) TROVAFLOXACIN ORAL SUSPENSIONS

(75) Inventors: Douglas J. M. Allen, New London; Daniel R. Arenson, East Lyme; S. Sonja Sekulic, Gales Ferry, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/565,420

(22) Filed: May 5, 2000

Related U.S. Application Data

(60) Provisional application No. 60/137,463, filed on Jun. 4, 1999.

(51) Int. Cl.[7] ........................ A61K 31/435; C07D 471/04
(52) U.S. Cl. .............................................. 514/300; 546/123
(58) Field of Search .............................. 546/123; 514/300

(56) References Cited

U.S. PATENT DOCUMENTS

| 5,164,402 | 11/1992 | Brighty ................................ 514/300 |
| 5,229,396 | 7/1993 | Brighty ................................ 514/300 |
| 5,266,559 | 11/1993 | Brighty ............................ 514/229.8 |
| 5,391,763 | 2/1995 | Brighty ................................ 548/515 |
| 5,633,006 | 5/1997 | Catania et al. ...................... 424/441 |
| 5,763,454 | 6/1998 | Handanyan et al. ................ 514/300 |

FOREIGN PATENT DOCUMENTS

WO9639406  12/1996  (WO).
WO9707800   3/1997  (WO).

OTHER PUBLICATIONS

Physicians' Desk Reference (PDR), pp. 2414–2421(1999).

*Primary Examiner*—Bernard Dentz
(74) *Attorney, Agent, or Firm*—Peter C. Richardson; Gregg C. Benson; Jennifer A. Kispert

(57) ABSTRACT

This invention relates to suspensions for oral administration comprising novel trovafloxacin zwitterionic crystals, and processes for preparing such crystals. This invention further relates to other pharmaceutical compositions comprising these novel crystals, and to methods of using these suspensions, and these novel crystals in such other dosage forms, for treating bacterial infections in mammals.

47 Claims, No Drawings

TROVAFLOXACIN ORAL SUSPENSIONS

CROSSREFERENCE TO RELATED APPLICATION

This application claims priority from U.S. Provisional Patent Application Ser. No. 60/137,463 filed Jun. 4, 1999, the benefit of which is hereby claimed under 37 C.F.R. §1.78(a)(3).

FIELD OF THE INVENTION

This invention provides oral suspensions comprising the antibiotic trovafloxacin. This invention also provides novel trovafloxacin zwitterionic crystals. In addition, this invention provides novel processes for preparing such crystals. Further, this invention provides methods of using these suspensions, and these novel crystals in other dosage forms, for treating bacterial infections.

BACKGROUND OF THE INVENTION

Trovafloxacin is a known quinolone antibacterial of Formula I

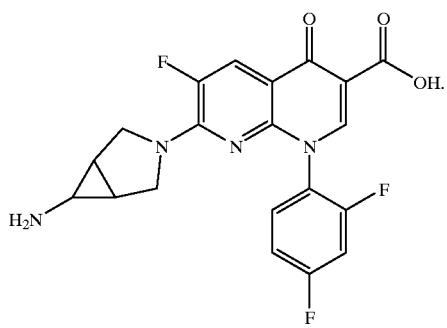

Trovafloxacin has the chemical name: (1α, 5α, 6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxylic acid.

Trovafloxacin, and salts and related derivatives thereof, and their antibacterial activities, are disclosed in U.S. Pat. Nos. 5,164,402; 5,229,396; 5,266,569; 5,391,763; and 5,763,454; and in International PCT Application Nos.

PCT/US95/07211 published as WO 96/39406 and IB/96/00756 published as WO 97/07800.

Trovafloxacin is available as a particular trovafloxacin acid addition salt, namely, trovafloxacin mesylate (TABLET), for oral administration and as alatrofloxacin (prodrug) mesylate for intravenous administration. (Physicians' Desk Reference (PDR), 53rd Ed., Medical Economics Co., Inc., Montvale, N.J., pages 2414–2421 (1999)).

Chemically, as discussed above, trovafloxacin mesylate, a fluoronaphthyridone related to the fluoroquinolone antibacterials, is (1α, 5α, 6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxylic acid, monomethanesulfonate, of the Formula III

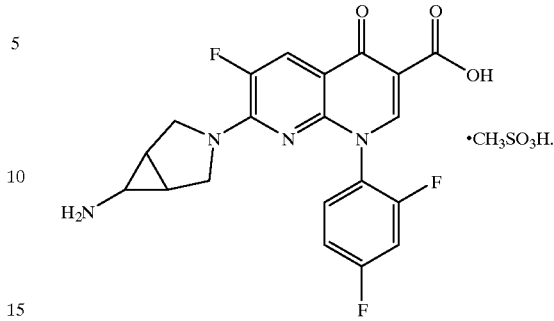

The TABLETS are available as 100 mg and 200 mg (trovafloxacin equivalent) blue, film-coated tablets, and also contain microcrystalline cellulose, crosslinked sodium carboxymethyl cellulose and magnesium stearate. The TABLET coating is a mixture of hydroxypropylcellulose, hydroxypropylmethylcellulose, titanium dioxide ($TiO_2$), polyethylene glycol and FD&C blue #2 aluminum lake.

Oral dosage forms of pharmaceutical agents are generally preferred because they provide for easy, low-cost administration which generally encourages patient compliance. However, certain pharmaceutical agents, e.g., penicillin, ampicillin and erythromycin, exhibit the undesirable characteristic of bitter taste either during or immediately after oral administration which generally discourages patient compliance, particularly by pediatric patients.

Generally, sweetening agents such as sucrose, as well as flavoring agents, are added to such orally administered pharmaceutical compositions to mask such bitter taste and aftertaste. Other taste-masking agents are also known such as those described in U.S. Pat. No. 5,633,006 which discloses the use of an alkaline earth oxide in a liquid suspension pharmaceutical composition to mask the bitter taste and/or aftertaste of the bitter flavor of a bitter pharmaceutical agent. Alternatively, it is also known in the art to mask such bitterness by microencapsulating the unpleasant tasting active agent in a coating of ethyl cellulose, or other cellulose derivatives, to provide chewable taste-masked dosage forms.

As discussed above for certain pharmaceutical agents, solutions of trovafloxacin have also been identified as exhibiting the undesirable characteristic of bitter taste either during or immediately after oral administration. The TABLETS contain a salt of trovafloxacin, rather than a trovafloxacin zwitterion, and are suitably buffered to overcome such taste issues; however, tablets are not always the preferred dosage form, e.g., for pediatric patients, and for patients who are unable to swallow tablets.

This invention overcomes the taste issues associated with such solutions of trovafloxacin by providing liquid suspensions comprising novel trovafloxacin zwitterionic crystals which, by virtue, in part, of their unexpected physical and chemical stabilities, enable the preparation of substantially homogenous suspensions. The provision of such substantially homogenous suspensions enable accurate dosing.

Furthermore, the provision of easily pourable homogeneous suspensions also facilitates oral administration since, for example, no other fluid need be consumed simultaneously as is typically done with a tablet dosage form. Moreover, a certain population of patients, specifically pediatric patients, are generally more receptive to a fluid that they can see and swallow, or mix into food (where suitable), versus a tablet or a needle. Further yet, the health care provider, e.g., parent or physician, administering the medicine to a pediatric patient in the form of a liquid lessens both choking concerns (with respect to a tablet) and the dangers of handling a needle and syringe (with respect to an injection). Also, administration to large numbers of patients at once is easier, e.g., no fluid to wash down the tablet is necessary, and generates less waste, e.g., packaging of a suspension versus individual sterile syringes and needles for each patient.

While this invention does not intend to preclude the utility of dissolving a TABLET in a suitable pharmaceutically acceptable buffer, and the oral administration thereof; nonetheless, the liquid suspension pharmaceutical compositions of this invention provide the advantage of being ready for immediate administration as supplied. Moreover, because of the aforementioned physical and chemical properties of the novel trovafloxacin zwitterionic crystals comprising the suspensions of this invention, these suspensions, unlike suspensions in general, resuspend very quickly upon shaking, and resettle very slowly, which collectively allow for desirable homogeneity over a period of time suitable for oral administration.

A novel crystal form of a salt of trovafloxacin, i.e., trovafloxacin mesylate, methods of using the compound for the treatment of bacterial infections in mammals, especially humans, and pharmaceutical compositions comprising the compound, are disclosed in the aforementioned U.S. Pat. No. 5,763,454.

In contrast, novel trovafloxacin zwitterionic (versus salt) crystal forms are disclosed in the aforementioned WO 97/07800 of Formula II

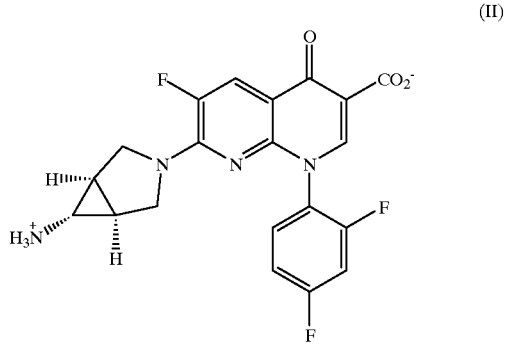

(II)

selected from the group consisting of its crystalline non-hygroscopic (polymorph PI) and hygroscopic (polymorph PII) polymorphs and a pentahydrate, methods for their preparation, e.g., from a metastable form of trovafloxacin zwitterion (a needle form), and methods for treating bacterial infections in mammals by administering said compounds, e.g., as a suspension. A TABLET, dissolved in a suitable aqueous buffer, e.g., sodium bicarbonate, contains crystals of the needle form.

This invention provides additional novel trovafloxacin zwitterionic crystals, specifically a blade form and both a four-sided and a six-sided lath form, with the six-sided lath form being preferable. The aforementioned known needle form, as well as the novel blade and four-sided laths, all convert in an aqueous medium, over various periods of time, into the novel six-sided laths. This invention also provides novel processes for preparing the blade and lath crystals of this invention from the aforementioned known needle form. This invention further provides novel processes for converting between the blade and lath forms. Further, the crystals of the needle form, prepared from dissolving a TABLET in a suitable aqueous buffer, will convert over time to the six-sided lath form.

The oral administration of suspensions comprising these novel trovafloxacin zwitterionic crystals results in no appreciable bitter taste or aftertaste. In addition, once resuspended, these crystals tend to remain in suspension rather than settle out, which enables more accurate dosing. Moreover, the suspensions of this invention provide a more desirable dosage form for certain patients, e.g., children and the elderly.

This invention also provides methods for treating bacterial infections by administering such crystals or suspensions comprising such crystals.

SUMMARY OF THE INVENTION

The present invention is based on the discovery that a liquid pharmaceutical composition or suspension comprising a novel crystalline form of trovafloxacin zwitterion of a blade form, or a four-sided lath form, or a six-sided lath form, and preferably of a six-sided lath form, can be orally administered without any appreciable bitter taste or aftertaste. These suspensions provide the patient with an alternate dosage form in addition to a TABLET or an alatrofloxacin (prodrug) mesylate injection.

In a first aspect, this invention provides a novel crystalline trovafloxacin zwitterion of a six-sided lath form, characterized by exhibiting the following X-ray wet cake diffraction pattern

| Peak no. | 1 | 2 | 3 | 4 | 5 | 6 | 7 | 8 | 9 |
|---|---|---|---|---|---|---|---|---|---|
| 2θ(°) Cu | 6.2 | 8.6 | 11.8 | 12.4 | 12.8 | 16.1 | 16.8 | 18.6 | 19.5 |
| d space | 14.3 | 10.0 | 7.5 | 7.1 | 6.9 | 5.5 | 5.3 | 4.8 | 4.5 |
| Peak no. | 10 | 11 | 12 | 13 | 14 | 15 | 16 | 17 | 18 |
| 2θ(°) Cu | 20.1 | 22.6 | 23.7 | 26.7 | 28.3 | 29.9 | 37.7 | 39.0 | |
| d space | 4.4 | 4.1 | 3.8 | 3.3 | 3.2 | 3.0 | 2.4 | 2.3 | |

Where, as discussed above, a TABLET is dissolved in a suitable aqueous buffer (an aqueous buffer which adjusts the pH to from about pH 4 to about pH 11, e.g., sodium bicarbonate), resulting in trovafloxacin zwitterion of a needle form, these needles will convert, with time, e.g., weeks, to the novel six-sided laths. However, given that a dissolved TABLET would generally be prepared as such for immediate oral administration, coupled with the lack of a preservative in the TABLET, not enough time would most likely pass to allow for the conversion from such needles to the six-sided laths prior to oral administration.

In a second aspect, this invention provides a novel crystalline trovafloxacin zwitterion/hydrate of a four-sided lath form, characterized by the following crystal parameters derived from standard single crystal X-ray crystallographic analysis: formula—$C_{20}H_{15}N_4O_3F_3$ (zwitterion), $C_{20}H_{14}N_4O_3F_3{}^-Na^+ \cdot 4.75H_2O$ (512.9); cell dimensions—a=11.202 (2) Å, b=15.2630 (1) Å, c=15.8910 (1) Å, α=103.24 (1)°, β=110.02 (1)°, γ=108.71 (1)°, V=2235.8 (4) Å$^3$; and space group—P1 bar.

In a third aspect, this invention provides a novel crystalline trovafloxacin zwitterion of a blade form, characterized by exhibiting the following X-ray powder diffraction pattern

| Peak no. | 1 | 2 | 3 | 4 | 5 | 6 | 7 | 8 | 9 |
|---|---|---|---|---|---|---|---|---|---|
| 2θ(°) Cu | 6.3 | 9.8 | 11.7 | 12.4 | 13.9 | 15.5 | 16.5 | 17.1 | 18.1 |
| d space | 14.1 | 9.1 | 7.5 | 7.2 | 6.4 | 5.7 | 5.4 | 5.2 | 4.9 |
| Peak no. | 10 | 11 | 12 | 13 | 14 | 15 | 16 | 17 | 18 |
| 2θ(°) Cu | 19.3 | 20.3 | 21.8 | 22.3 | 22.9 | 23.9 | 24.9 | 26.4 | |
| d space | 4.6 | 4.4 | 4.1 | 4.0 | 3.9 | 3.7 | 3.6 | 3.4 | |

In a fourth aspect, this invention provides novel processes for preparing the aforementioned laths and blades. The laths and blades can be prepared from the aforementioned needles. The laths can be prepared from the needles directly or where the needles are first converted to the blades. The blades can also be prepared from the laths.

This invention provides novel processes for preparing the six-sided laths from the needles comprising the steps, in sequence, of: preparing an aqueous solution of a trovafloxacin acid addition salt; precipitating the zwitterion from said salt by adjusting the pH of said aqueous solution to a pH of from about pH 4 to about pH 10; and maintaining said solution at ambient temperature for a period of time. A preferred pH is from about pH 4 to about pH 7. A preferred amount of trovafloxacin acid addition salt is from about 10 mg/mL to about 200 mg/mL. A particularly preferred amount of trovafloxacin acid addition salt is from about 35 mg/mL to about 120 mg/mL. An especially preferred amount of trovafloxacin acid addition salt is about 100 mg/mL. The trovafloxacin acid addition salt is added to water at a preferred temperature of from about 5° C. to about 40° C.; at a particularly preferred temperature of from about 15° C. to about 30° C.; and at an especially preferred temperature of from about 25° C. to about 30° C.

This invention provides other processes for preparing the six-sided laths from the needles by way of the blades, by adding heating and cooling steps to the processes described immediately above. More specifically, the processes comprise the steps, in sequence, of: preparing an aqueous solution of a trovafloxacin acid addition salt; precipitating the zwitterion from said salt by adjusting the pH of said aqueous solution to a pH of from about pH 4 to about pH 10, at a first temperature of at least about 70° C.; and cooling said solution to a second temperature of less than about 70° C. A preferred pH is from about pH 4 to about pH 7.

This invention provides yet other processes for preparing the six-sided laths from the needles by way of the blades and the four-sided laths, comprising preparing an aqueous solution of a trovafloxacin acid addition salt; precipitating the zwitterion from said salt by adjusting the pH of said aqueous solution to a pH of from about pH 9 to about pH 12, at a first temperature of at least about 70° C.; and cooling said solution to a second temperature of less than about 70° C. After said cooling, and before said period of time passes to generate the aforementioned six-sided laths (e.g., from about 2 days to about 5 days), the crystals convert from the blades to the novel four-sided laths (e.g., from about 12 hours to about 36 hours). A preferred pH is about pH 9.5.

This invention also provides for the conversion of any of the six-sided lath preparations provided in this disclosure to the blades by heating the solutions comprising the laths to a temperature of at least about 70° C.

Even less bitter taste or aftertaste is reported for crystal preparations of this invention adjusted to a final pH of from about pH 6 to about pH 8, and preferably about pH 7. Hence, it is preferred that the resultant crystal preparations comprise the additional step, where necessary, of adjusting the pH to from about pH 6 to about pH 8, and preferably about pH 7.

In a fifth aspect, this invention provides pharmaceutical compositions comprising a novel trovafloxacin zwitterionic crystal of the four-sided or the six-sided lath forms, or the blade form, and a pharmaceutically acceptable carrier, vehicle or diluent. In a particularly preferred embodiment, this invention provides pharmaceutical compositions for oral administration. In an especially preferred embodiment, this invention provides liquid pharmaceutical compositions for oral administration.

In another especially preferred embodiment of said fifth aspect, this invention provides suspensions for oral administration comprising an antibacterially effective amount of a novel trovafloxacin zwitterionic crystal of the blade form, or of the four-sided lath form or the six-sided lath form, and a pharmaceutically acceptable carrier, vehicle or diluent, where pharmaceutically acceptable means that the carrier, diluent, vehicle, excipients, and/or salt must be compatible with the other ingredients of the formulation, and not deleterious to the recipient thereof, provided that, where said suspension comprises said four-sided lath form or said six-sided lath form, said suspension comprises an amount of water sufficient to maintain said lath form. The suspensions optionally further include one or more suspending agents, one or more anti-caking agents, one or more preservatives, one or more buffering agents, one or more sweetening agents, and one or more flavoring agents.

A preferred suspension comprises trovafloxacin zwitterion of the six-sided lath form, a suspending agent, an anti-caking agent, a combination of preservatives, and a combination of buffering agents, and has a pH of from about pH 6 to about pH 8.

Another preferred suspension comprises trovafloxacin zwitterion of the six-sided lath form, a suspending agent, an anti-caking agent, a combination of preservatives, a combination of buffering agents, a sweetening agent, and a flavoring agent, and has a pH of from about pH 6 to about pH 8.

A particularly preferred suspension comprises from about 1 mg/mL to about 40 mg/mL trovafloxacin zwifterion of the six-sided lath form, from about 0.05 weight % to about 1.0 weight % of xanthan gum, from about 0.01 weight % to about 2.0 weight % of colloidal silicon dioxide, from about 0.5 mg/mL to about 3.0 mg/mL of methyl paraben, from about 0.05 mg/mL to about 0.3 mg/mL of propyl paraben, from about 0.05 mg/mL to about 0.2 mg/mL of butyl paraben, from about 5 mM to about 100 mM of a combination of sodium phosphate dibasic anhydrous and sodium phosphate monobasic monohydrate, from about 10 weight % to about 60 weight % of sucrose, and from about 0.01 weight % to about 1.0 weight % of strawberry flavoring, and has a pH of from about pH 6.7 to about pH 7.3.

An especially preferred suspension comprises from about 10 mg/mL to about 20 mg/mL trovafloxacin zwitterion of the six-sided lath form, from about 0.20 weight % to about 0.30 weight % of xanthan gum, from about 0.05 weight % to about 0.20 weight % of colloidal silicon dioxide, from about 0.5 mg/mL to about 3.0 mg/mL of methyl paraben, from about 0.05 mg/mL to about 0.3 mg/mL of propyl paraben, from about 0.05 mg/mL to about 0.2 mg/mL of butyl paraben, from about 5 mM to about 100 mM of a combination of sodium phosphate dibasic anhydrous and sodium phosphate monobasic monohydrate, from about 10 weight % to about 30 weight % of sucrose, and from about 0.03 weight % to about 0.6 weight % of strawberry flavoring, and has a pH of about 7.

Also provided are aqueous suspensions comprising a crystal as defined in said first aspect and an amount of water sufficient to maintain said six-sided lath form of said crystal, and those comprising a crystal as defined in said second aspect and an amount of water sufficient to maintain said four-sided lath form of said crystal.

In a sixth aspect, this invention provides methods for treating a bacterial infection in a mammal comprising administering to said mammal an antibacterially effective amount of a novel crystalline trovafloxacin zwitterion of a blade form, or of a four-sided lath form or of a six-sided lath form, where treating includes, inter alia, preventative (e.g., prophylactic), palliative and curative treatment.

All of the documents cited herein, including the foregoing, are incorporated by reference herein in their entireties.

DETAILED DESCRIPTION OF THE INVENTION

Unless otherwise noted, throughout this document: % is percent, °C. is degrees-Celsius, d is day or days, g is gram or grams, h is hour or hours, kg is kilogram or kilograms, L is liter or liters, mg is milligram or milligrams, min is minute or minutes, mL is milliliter or milliliters, mM is millimolar (concentration), N is normal (concentration), $NaHCO_3$ is sodium bicarbonate, NaOH is sodium hydroxide, RT is room temperature and rpm is revolutions per minute.

As discussed above, this disclosure provides several novel processes for preparing the novel trovafloxacin zwitterionic crystals, and the use thereof in liquid suspension pharmaceutical compositions for the treatment of bacterial infections.

Most of these processes begin by the step of adding a trovafloxacin acid addition salt to water, with stirring, where necessary, to maintain homogeneity. Any suitable acid addition salt can be used in the processes of this invention. Suitable anions of such acid addition salts include, for example, mineral acids such as hydrobromic, hydrochloric, hydroiodic, sulfuric, nitric and phosphoric; organic acids such as sulfamic, sulfonic, e.g., benzenesulfonic (besylate), p-toluenesulfonic (tosylate), methanesulfonic (mesylate) and trifluoromethanesu Ifonic (trifluoromesylate); and carboxylic acids such as acetic, ascorbic, benzoic, cinnamic, citric, fumaric, gluconic, maleic, malic, proprionic, succinic, and tartaric. Mesylate is a preferred anion.

Then, the pH of the aqueous solution comprising the trovafloxacin zwitterion of the needle form is measured and adjusted to a pH which depends upon the particular process being used. For example, where the six-sided laths are prepared directly from the needles, the pH is adjusted to at least about pH 4 to about pH 10, preferably from about pH 6 to about pH 8, and most preferably to about pH 7. However, adjusting the pH to between pH 4 and pH 5, and preferably pH 4.3, expedites, e.g., days versus weeks, the conversion of the needles to the laths. Where such a low pH is used for such expediting, the resultant solution, after the conversion is complete, is then adjusted to a pH of from about pH 6 to about pH 8, and preferably about pH 7. In addition, where the six-sided laths are prepared from the needles through the blades and the four-sided laths, in that order, the pH is adjusted to from about pH 9 to about pH 12, and preferably about pH 9.5. Those skilled in the art will understand from this disclosure how to adjust the pH of the aqueous solution comprising the trovafloxacin zwitterion to form the desired crystal forms for any given situation. Where the process used is the process of preparing the six-sided laths from the needles through the blades and the four-sided laths, NaOH is the preferred base for adjusting the pH to from about pH 9 to about pH 12. A preferred concentration of such NaOH is from about 1% to about 20%. A particularly preferred concentration of such NaOH is about 10%.

As those skilled in the art will appreciate, any suitable material capable of effecting a pH change can be used in the processes of the present invention, or to adjust the pH of any suspension of this invention, e.g., any suitable acid or base may be used to adjust the pH of the aqueous solution of trovafloxacin zwifterion, as well as for any other step in any of the novel processes of this invention requiring a pH adjustment, and further including the neutralizing, e.g., with $NaHCO_3$, of a TABLET to create trovafloxacin zwitterion. Suitable bases include inorganic bases such as alkali or alkaline earth hydroxides, carbonates and bicarbonate, phosphates, and organic bases such as citrate, tri($C_{1-6}$)alkyl amines, pyridine and morpholine. For example, sodium citrate, sodium bicarbonate, sodium hydroxide, potassium hydroxide, calcium phosphate, or magnesium sulfate can be used to raise the pH, while hydrochloric acid or sulfuric acid can be used to lower the pH. In addition, any suitable manner of determining the pH can be used in the processes of the present invention including, for example, the dipping of pH test strips into the solutions of the processes, or the use of a suitable pH meter.

In addition to the process of this invention for preparing the six-sided laths directly from the needles, this invention also provides processes for preparing the six-sided laths from the needles but passing through a conversion to blades before the six-sided laths. The blades are prepared from the needles by heating the needles preparation. More specifically, the aforementioned precipitation of the zwitterion from the salt in the aforementioned aqueous solution comprising the trovafloxacin zwitterion of the needle form, is performed at a temperature of at least about 70° C. The heated solution is then cooled to a temperature of less than about 70° C., and preferably to RT. The cooling of the solution comprising the blades allows for the conversion of those blades to the six-sided laths. The blades of this invention, in contrast to the needles and laths, need not be kept hydrated to retain their crystalline structure, i.e., the blades can be isolated while the needles and laths convert to other crystalline structures upon dehydration.

As those skilled in the art will understand in light of the present disclosure, X-ray data for the "non-isolatable forms," i.e., the four-sided and six-sided lath forms, can be obtained by doing a rapid scan on a wet filtered cake. Moreover, those skilled in the art will also understand how to ascertain at what point the wet filtered cake (or filtered paste) begins to convert to another form so that one may obtain an X-ray before such conversion. For example, such a conversion point can be determined using standard Polarized Light Microscopy. The aforementioned conversion points of the four-sided and six-sided lath forms of this invention are readily determined from a water suspension within which they reside as the water does not substantially evaporate for a period of time suitable for such determination. Moreover, those skilled in the art will appreciate from the present description the amount of water suitable to maintain either a four-sided lath form or a six-sided lath form of this invention at any given juncture for any given amount of time. For example, those skilled in the art will understand that it would be disadvantageous to allow the surface area of the crystal to dry to any appreciable extent.

The heat can be applied to the aqueous solution in any suitable manner and, as described in the EXAMPLES provided hereinbelow, the use of a heating mantle is generally convenient.

Likewise, any method of cooling can be used in the processes of this invention, e.g., standing at RT, an ice bath, a cold room, or simply removing the heating source. Those skilled in the art will understand from the present description that the conversion points for any given process of this invention which comprises a cooling step may be manipulated to some extent by the selected rate of cooling. For example, the reaction can be cooled over a suitably extended period of time, e.g., about 30 min, or it can be cooled over a suitably brief period of time, e.g., a few minutes, and then maintained for a suitable period of time, e.g., about 24 h, to achieve the extent of conversion desired. As discussed above, those skilled in the art can monitor the progress and extent of conversion for any given process of this invention using, e.g., standard Polarized Light Microscopy.

Those skilled in the art will appreciate from this disclosure that the periods of time described for any step of any given process(es) of this invention are dependent, in part, for example, upon parameters such as, e.g., pH, temperature, and concentration, and the like, and also, based upon the present disclosure, will be able to select suitable parameters (such as these) to achieve any desired result. Such modifications are considered within the scope of the present invention and accordingly, are deemed within the scope of the appendant claims.

Any of the novel trovafloxacin zwitterionic crystals of this invention can be used in the suspensions of this invention. The novel crystals can also be administered in any other suitable dosage form (e.g., tablets, solutions for injection), and those skilled in the art will understand how to prepare any suitable dosage form based upon standard pharmaceutical practice in light of the present disclosure. However, as discussed earlier, this invention is primarily directed to the provision of liquid suspension pharmaceutical compositions for oral administration.

It is preferred that the suspensions of this invention comprise the six-sided lath form because the six-sided lath form is the most stable of the forms discussed herein in an aqueous environment at about RT, i.e., all of the other forms convert to the six-sided laths in aqueous medium at RT. In addition, it is also preferred that the pH of the suspension be from about pH 6 to about pH 8, more preferably from about pH 6.7 to about pH 7.3, and most preferably about pH 7. Moreover, it is also preferred that the pharmaceutically acceptable carrier, vehicle, or diluent of the suspension be water.

Any suitable amount of any of the novel zwitterionic forms can be used in the suspensions of this invention, and those skilled in the art will understand how to adjust such amount for any given situation, e.g., dosage regimen, or patient. For example, those skilled in the art will understand how much of the zwitterion will be suitable for any given patient depending upon, for example, the type(s) of bacterium(a) the patient is infected with, the volume of suspension convenient to orally administer (e.g., from about 0.5 mL to about 20 mL), and the potency of the zwitterion. A preferred amount of the zwitterion of this invention is from about 1 g/mL to about 40 mg/mL. A more preferred amount of the zwitterion of this invention is from about 10 mg/mL to about 20 mg/mL.

As those skilled in the art will appreciate, as exemplified by standard pharmaceutical practice, e.g., formulation art, any suitable additional components can be added to the suspensions of this invention as desired for any given situation. As more fully described below, preferred additional components include suspending agents, anti-caking agents, preservatives, buffering agents, sweetening agents, flavoring agents, pH adjusting agents, and coloring agents such as, for example, vegetable dyes, or pigments, e.g., $TiO_2$ generally in combination with non-ionic plasticizers such as polysorbate 60, polysorbate 80, polyvinyl pyrrolidone, and propylene glycol. As those skilled in the art will appreciate, the amounts of these agents that are actually used in any particular suspension are dependent upon, in large part, the exact agent selected and the other components of the given suspension. Those skilled in the art will understand based upon this disclosure which agent(s) to select and what amount(s) of such agent(s) to include in any given suspension.

The suspensions of this invention may further include one or more suspending agents (also referred to in the art as "viscosity agents" or as "thickening agents") in any suitable concentration. Any suitable suspending agent, or suitable combination of suspending agents, can be used in the suspensions of this invention. Suitable suspending agents include, for example, hydrocolloid gums, e.g., xanthan gum, guar gum, locust bean gum, gum tragacanth, and the like. Additional suitable suspending agents include synthetic agents such as, for example, aluminum stearate, methyl cellulose, sodium carboxymethylcellulose, polyvinylpyrrolidone, hydroxypropyl-cellulose, hydroxypropylmethylcellulose, and the like. Xanthan gum is a preferred suspending agent. A preferred amount is from about 0.05 weight % to about 1.0 weight % based on the total weight of the suspension. A more preferred amount is from about 0.20 weight % to about 0.30 weight %.

Those skilled in the art will understand that it is advantageous to include an anti-caking agent in suspensions comprising a suspending agent. Any suitable anti-caking agent, or suitable combination of anti-caking agents, can be used in the suspensions of this invention. A preferred anti-caking agent is colloidal silicon dioxide. Those skilled in the art will understand how to select a suitable amount of colloidal silicon dioxide for any given suspension, i.e., an amount such that a firm, difficult to resuspend (beyond mild physical agitation) cake does not form under normal conditions of transportation and storage, but not an amount which causes gelation. A preferred amount of anti-caking agent is from about 0.01 weight % to about 2.0 weight % based on the total weight of the suspension. A more preferred amount of anti-caking agent is from about 0.05 weight % to about 0.20 weight %.

Any suitable preservative, or suitable combination of preservatives, can be used in the suspensions of this invention. As with the other optional components of the suspensions of this invention, those skilled in the art will appreciate that the amount of preservative used in any particular suspension is a function of, in large part, the exact preservative used, the pH of the suspension, and the other components comprising the given suspension. Suitable preservatives for inclusion in the suspensions of this invention include, for example, parabens, benzyl alcohol, sodium benzoate, phenol, benzalkonium chloride, thimerosal, chlorobutanol, benzoic acid, sodium bisulfite, and sodium proprionate. Parabens are preferred preservatives. For example, a preferred amount of methyl paraben is from about 0.5 mg/mL to about 3.0 mg/mL based on the weight of the suspension, of propyl paraben is from about 0.05 mg/mL to about 0.3 mg/mL based on the weight of the suspension, and of butyl paraben is from about 0.05 mg/mL to about 0.2 mg/mL based upon the weight of the suspension.

Any suitable buffering agent, or suitable combination of buffering agents, can be used in the suspensions of this invention. Suitable buffering agents include, for example, sodium phosphate dibasic anhydrous, sodium phosphate monobasic monohydrate, and combinations thereof. Preferred buffering agents include a combination of sodium phosphate dibasic anhydrous and sodium phosphate monobasic monohydrate. A preferred amount of buffering agent(s) is from about 5 mM to about 100 mM, such that the pH of the suspension, given all of the components of the suspension, has a pH of from about pH 6 to about pH 8, preferably from about pH 6.7 to about pH 7.3, and most preferably about pH 7. A more preferred amount is from about 10 mM to about 30 mM.

Any suitable sweetening agent, or suitable combination thereof, can be used in the suspensions of this invention. Suitable sweetening agents include, for example, sucrose, fructose, glucose, sorbitol, and artificial sweetening agents, e.g., aspartame, saccharin and xylitol. Sucrose is a preferred sweetening agent. A preferred amount of sweetening agent is from about 10 weight % to about 60 weight %, based upon the total weight of the suspension. A more preferred amount of sweetening agent is from about 10 weight % to about 30 weight %.

Any suitable flavoring agent, or suitable combination thereof, can be used in the suspensions of this invention. Suitable flavoring agents include, for example, synthetic flavor oils and flavoring aromatics and/or natural oils, extracts from plant leaves, flowers, fruits, and so forth and combinations thereof. Suitable oils include, for example, cinnamon oil, oil of wintergreen, peppermint oils, clove oil, bay oil, anise oil, eucalyptus oil, thyme oil, cedar leaf oil, oil of nutmeg, oil of sage, oil of bitter almonds, and cassia oil. Additional suitable flavoring agents include, for example, vanilla, citrus oil (e.g., lemon, orange, grape, lime, grapefruit), citric acid, menthol, glycine, orange powder, cream, chocolate, mocha, spearmint, and cola. Suitable flavor essences include, for example, apple, apricot, banana, cherry, peach, pear, pineapple, plum, raspberry and strawberry. Any suitable bubblegum flavoring may also be used in the suspensions of this invention. Strawberry flavor is a preferred flavoring agent. A preferred amount of flavoring agent is from about 0.01 weight % to about 1.0 weight %, based on the total weight of the suspension. A more preferred amount of flavoring agent is from about 0.30 weight % to about 0.60 weight %.

Preferred suspensions of this invention further comprise one or more suspending agents, one or more anti-caking agents, one or more preservatives, one or more buffering agents, one or more flavoring agents, and one or more sweetening agents. Particularly preferred are suspensions comprising xanthan gum, colloidal silicon dioxide, a combination of methyl, propyl and butyl paraben, a combination of sodium phosphate dibasic anhydrous and sodium phosphate monobasic monohydrate, and sucrose, and strawberry flavoring.

As discussed above, the suspension formulations of this invention are prepared using standard pharmaceutical formulation practice. Moreover, the activity, methods for testing activities, dosages, dosage forms, methods of administration and background information concerning trovafloxacin are set forth in the aforementioned issued patents and pending international applications, as well as in the PDR for TABLETS and alatrofloxacin (prodrug) mesylate for intravenous administration. Generally, the preferred oral suspensions of this invention will contain the equivalent of from about 100 to about 300 mg trovafloxacin zwitterionic crystal for non-pediatric patients, and from about 2 to about 5 mg per weight (kg) for pediatric patients, each in a suitable volume.

Oral administration of the formulations of this invention is achieved according to the normal oral mode of administration, the suspension is imbibed. Alternatively, the suspension may be mixed with foods and drinks where suitable. Further yet, any other suitable method of oral administration is considered part of this invention.

As discussed above, the issued patents, pending international applications and the relevant scientific and medical literature, e.g., the PDR, all of which are incorporated in the entireties herein, together with standard pharmaceutical practice and procedure, in light of the present disclosure, can be used by those skilled in the art to prepare the different crystal forms of the trovafloxacin zwitterion and the pharmaceutical compositions (in particular, the liquid suspensions) comprising the zwitterion, as well as, to treat mammals by administering antibacterially effective amounts of the zwitterion to such mammals. Preferred mammals include human beings and companion animals. Particularly preferred mammals are human beings.

The following EXAMPLES are provided solely for the purposes of illustration and do not limit the invention which is defined by the appendant claims.

It will also be understood that other changes and modifications that may be practiced are also part of this invention and, as such, are within the scope of the appendant claims.

EXAMPLES

Example 1

Preparation of Needles.

Sterile water (2.64 kg) was placed into a 22L round bottom flask, a mesylate salt of trovafloxacin (123.2 g) was added with stirring, and the flask was protected from light. The solution was stirred for 10 min. The pH was adjusted to pH 7.3 by adding 10% NaOH (about 91 g, w/w) over 1 to 2 min, and then by adding 1% NaOH (about 48 g, w/w) over 1 to 2 minutes until the pH was 7.3. The solution was stirred for 20 min (protected from light), and the pH maintained at pH 7.3, forming a wet slurry comprising the zwitterionic crystals of the needle form which gave the characteristic X-ray powder diffraction pattern provided above.

Example 2

Preparation of Six-sided Laths Directly From Needles.

Needles were prepared in an analogous manner to that described in EXAMPLE 1. The needles were then allowed to sit at RT for about 6 weeks. The resultant crystals gave the characteristic X-ray powder diffraction pattern for the six-sided laths provided above.

Example 3

Preparation of Blades Directly From Needles.

Sterile water (2.64 kg) was placed into a 22L round bottom flask, a mesylate salt of trovafloxacin (123.2 g) was added with stirring, and the flask was protected from light. The solution was stirred for 10 min. The pH was adjusted to pH 7.3 by adding 10% NaOH (about 91 g, w/w) over 1 to 2 min, and then by adding 1% NaOH (about 48 g, w/w) over 1 to 2 min until the pH was 7.3, with heat to above 70° C. The solution was stirred for 20 min (protected from light), and the pH maintained at pH 7.3. The resultant crystals gave the characteristic X-ray powder diffraction pattern for the blades provided above.

Example 4
Preparation of Six-sided Laths From Blades.

Blades were prepared in an analogous manner to that described in EXAMPLE 3. The aqueous solution was allowed to cool. The resultant crystals gave the characteristic X-ray powder diffraction pattern for the six-sided laths provided above.

Example 5
Preparation of Four-sided Laths From Needles through Blades.

Sterile water (2.64 kg) was placed into a 22L round bottom flask, a mesylate salt of trovafloxacin (123.2 g) was added with stirring, and the flask was protected from light. The solution was stirred for 10 min. The pH was adjusted to above pH 9.5 by adding 10% NaOH (about 91g, w/w) over 1 to 2 min, and then by adding 1% NaOH (about 55g, w/w) over 1 to 2 min until the pH was above 9.5, with heat to above 70° C. The solution was cooled to RT, and allowed to stand at RT for about 24 hours. The resultant crystals gave the characteristic crystal parameters for the four-sided laths provided above.

Example 6
Preparation of Six-sided Laths From Four-sided Laths.

Four-sided laths were prepared in an analogous manner to that described in EXAMPLE 5, and then the solution was allowed to stand at RT for an additional 5 d. The resultant crystals gave the characteristic X-ray powder diffraction pattern for the six-sided laths provided above.

Example 7
Preparation of Blades From Six-sided Laths.

The experiment was performed in triplicate, i.e., the six-sided laths were prepared in an analogous manner to that described in EXAMPLES 2, 4 and 6. Each of the lath preparations was then heated to about 70° C. The resultant crystals gave the characteristic X-ray powder diffraction pattern for the blades provided above.

Example 8
Preparation of a Suspension Comprising Six-sided Laths.

Needles were prepared in an analogous manner to that described in EXAMPLE 1.

Sterile water (5.75 kg) was added to a 12L round bottom flask and heated to from about 67° C. to about 70° C. Methyl paraben (10.0 g), propyl paraben (2.0 g) and butyl paraben (1.0 g) were added to the flask. The solution was stirred until the parabens were dissolved, and then cooled to RT. Sodium phosphate dibasic anhydrous (28.2 g) and sodium phosphate monobasic monohydrate (14.0 g) were then added, followed by sucrose (2.0 kg) with stirring until the sucrose dissolved. The pH of the resultant excipient solution was maintained at pH 7.3. The excipient solution was then mixed into the solution comprising the needles. Strawberry flavor (60.0 g, density of 0.9354 g/mL) was added. The resultant suspension formulation was stirred and the pH of the suspension formulation was maintained at pH 7.3. The needles were maintained at RT, and converted to the six-sided laths in about 6 weeks. The resultant crystals gave the characteristic X-ray powder diffraction pattern for the six-sided laths provided above.

Example 9
Preparation of a Suspension Comprising Six-sided Laths.

A suspension of about 100 mg/mL of a mesylate salt of trovafloxacin in water was prepared at RT by mixing the trovafloxacin mesylate and water. With stirring at about 220 rpm, the pH of the suspension was adjusted to a pH of from about pH 4.0 to about pH 4.6 by adding 10% NaOH (92 mg) for each mL of the suspension over about 20 min, and stirring was increased accordingly to ensure uniform pH in the suspension. After 1 h of agitation, the suspension was allowed to stand unagitated for 24 h. During this period of time, in the wet slurry, the needles were converted to the six-sided laths. Full conversion was verified by X-ray powder diffraction and microscopy. The resultant crystals gave the characteristic X-ray powder diffraction pattern for the six-sided laths provided above. After the crystal form conversion, the pH of the suspension was adjusted to pH 7.3 with 1% NaOH.

An excipient solution was prepared in an analogous manner to that described in EXAMPLE 8.

The suspension was diluted with the excipient solution (1:9, suspension:excipient solution) to achieve a 10 mg/mL suspension of the six-sided laths.

Example 10
Preparation of a Suspension Comprising Six-sided Laths.

A suspension of about 100 mg/mL of a mesylate salt of trovafloxacin in water was prepared at RT by mixing the trovafloxacin mesylate (1.245 g) and water (7.862 g). With stirring at about 220 rpm, the pH of the suspension was adjusted to a pH of from about pH 4.0 to about pH 4.6 by adding 10% NaOH (0.9111 g) over about 20 min, and stirring was increased accordingly to ensure uniform pH in the suspension. After 1 h of agitation, the suspension was allowed to stand unagitated for 24 h (at which time full conversion had occurred). The suspension was then diluted to 35 mg/mL by the addition of water (18.726 g). The pH was adjusted to from about pH 6.8 to about pH 7.2 with about 0.480 g of 1% NaOH.

An excipient solution was prepared by adding methyl paraben (0.100 g), propyl paraben (0.020 g) and butyl paraben (0.010 g) to water (57.606 g), and stirring while heating to from about 67° C. to about 73° C. Stirring was continued for 1 h. The solution was cooled to from about 34° C. to about 40° C. Xanthan gum (0.271 g), sodium phosphate monobasic monohydrate (0.100 g), sodium phosphate dibasic anhydrous (0.350 g), sucrose (20.000 g) and colloidal silicon dioxide (0.108 g) were added to the solution which was stirred until these components dissolved.

The suspension and the excipient solution were combined. Strawberry flavor (0.600 g) was added with stirring. The pH was adjusted to from about pH 6.7 to about pH 7.3 with 1% NaOH or 1% HCl.

Example 11
Preparation of a Suspension Comprising Needles from a TABLET.

A TABLET (100mg) was added to water (100 mL) in a bottle, and allowed to disintegrate for 5 min. Sodium bicarbonate solution (10 mL; prepared by adding sodium bicarbonate (2.5g) to water (800 mL), and diluting to 1L with water) was then added with shaking. The resultant suspension contained 10 mg/mL of needles.

What is claimed is:

1. A trovafloxacin zwitterionic crystal of the Formula

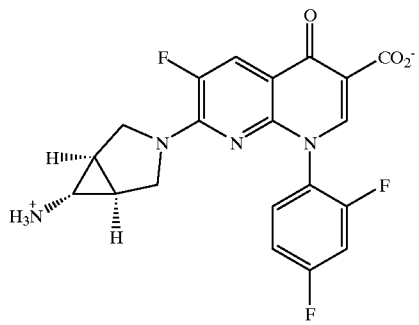

having a six-sided lath form, and exhibiting the following characteristic X-ray wet cake diffraction pattern

| Peak no. | 1 | 2 | 3 | 4 | 5 | 6 | 7 | 8 | 9 |
|---|---|---|---|---|---|---|---|---|---|
| 2θ(°) Cu | 6.2 | 8.6 | 11.8 | 12.4 | 12.8 | 16.1 | 16.8 | 18.6 | 19.5 |
| d space | 14.3 | 10.0 | 7.5 | 7.1 | 6.9 | 5.5 | 5.3 | 4.8 | 4.5 |

| Peak no. | 10 | 11 | 12 | 13 | 14 | 15 | 16 | 17 | 18 |
|---|---|---|---|---|---|---|---|---|---|
| 2θ(°) Cu | 20.1 | 22.6 | 23.7 | 26.7 | 28.3 | 29.9 | 37.7 | 39.0 | |
| d space | 4.4 | 4.1 | 3.8 | 3.3 | 3.2 | 3.0 | 2.4 | 2.3. | |

2. A trovafloxacin crystal having a four-sided lath form, and exhibiting the following characteristic X-ray crystal parameters: formula—$C_{20}H_{15}N_4O_3F_3$ (zwitterion), $C_{20}H_{14}N_4O_3F_3^-Na^+ \cdot 4.75H_2O$ (512.9); cell dimensions—a=11.202 (2) Å, b=15.2630 (1) Å, c=15.8910 (1) Å, α=103.24 (1)°, β=110.02 (1)°, γ=108.71 (1)°, V=2235.8 (4) Å$^3$; and space group—P1 bar.

3. A trovafloxacin zwitterionic crystal form of the Formula

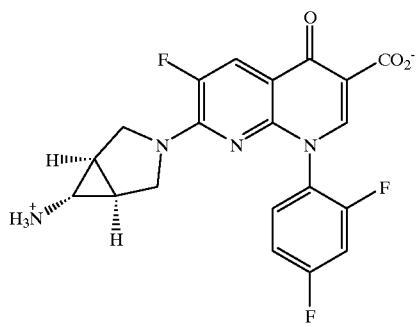

having a blade form, and exhibiting the following characteristic X-ray powder diffraction pattern

| Peak no. | 1 | 2 | 3 | 4 | 5 | 6 | 7 | 8 | 9 |
|---|---|---|---|---|---|---|---|---|---|
| 2θ(°) Cu | 6.3 | 9.8 | 11.7 | 12.4 | 13.9 | 15.5 | 16.5 | 17.1 | 18.1 |
| d space | 14.1 | 9.1 | 7.5 | 7.2 | 6.4 | 5.7 | 5.4 | 5.2 | 4.9 |

| Peak no. | 10 | 11 | 12 | 13 | 14 | 15 | 16 | 17 | 18 |
|---|---|---|---|---|---|---|---|---|---|
| 2θ(°) Cu | 19.3 | 20.3 | 21.8 | 22.3 | 22.9 | 23.9 | 24.9 | 26.4 | |
| d space | 4.6 | 4.4 | 4.1 | 4.0 | 3.9 | 3.7 | 3.6 | 3.4. | |

4. A process for preparing the crystal as defined in claim 1 comprising the steps, in sequence, of: preparing an aqueous solution of a trovafloxacin acid addition salt; precipitating said zwitterion from said salt by adjusting the pH of said solution to a pH of from about pH 4 to about pH 10; and maintaining said solution at ambient temperature for a period of time.

5. The process as defined in claim 4 wherein said trovafloxacin acid addition salt is trovafloxacin mesylate.

6. The process as defined in claim 4 wherein said pH is from about pH 6 to about pH 8, and said period of time is at least about 1 week.

7. The process as defined in claim 4 wherein said pH is from about pH 4 to about pH 4.6, and said period of time is less than about 24 h.

8. A process for preparing the crystal as defined in claim 2 comprising the steps, in sequence, of: preparing an aqueous solution of a trovafloxacin acid addition salt; precipitating said zwifterion from said salt by adjusting the pH of said solution to a pH of from about pH 9 to about pH 12, at a first temperature of at least about 70° C.; and cooling said solution to a second temperature of less than about 70° C.

9. The process as defined in claim 8 wherein said acid addition salt is trovafloxacin mesylate, said pH is adjusted with NaOH; said first temperature is about 70° C., and said second temperature is RT.

10. The process as defined in claim 8 further comprising, after said cooling, maintaining said solution for a period of time.

11. The process as defined in claim 10 wherein said second temperature is RT and said period of time is from about 12 to about 36 hours.

12. The process as defined in claim 10 wherein said acid addition salt is trovafloxacin mesylate, said pH is adjusted with NaOH; said first temperature is about 70° C., and said second temperature is RT.

13. The process as defined in claim 12 wherein said period of time is from about 12 to about 36 hours.

14. A process for preparing the crystal defined in claim 1 comprising the steps, in sequence, of: preparing an aqueous solution of a trovafloxacin acid addition salt; precipitating said zwitterion from said salt by adjusting the pH of said solution to a pH of from about pH 9 to about pH 12, at a first temperature of at least about 70° C.; cooling said solution to a second temperature of less than about 70° C., and maintaining said solution for a period of time of more than about 48 hours.

15. The process as defined in claim 14 wherein said acid addition salt is trovafloxacin mesylate, said pH is adjusted with NaOH; said first temperature is about 70° C., and said second temperature is RT.

16. The process as defined in claim 14 wherein said second temperature is RT and said period of time is about 5 days.

17. The process as defined in claim 16 wherein said acid addition salt is trovafloxacin mesylate, said pH is adjusted with NaOH; and said first temperature is about 70° C.

18. A process for preparing the crystal as defined in claim 3 comprising the steps, in sequence, of: preparing an aqueous solution of a trovafloxacin acid addition salt; and precipitating said zwitterion from said salt by adjusting the pH of said aqueous solution to a pH of from about pH 4 to about pH 10, at a temperature of at least about 70° C.

19. The process as defined in claim 18 wherein said trovafloxacin acid addition salt is trovafloxacin mesylate, said pH is about 7, and said temperature is about 70° C.

20. A process for preparing the crystal defined in claim 1 comprising the steps, in sequence, of: preparing an aqueous solution of a trovafloxacin acid addition salt; precipitating said zwitterion from said salt by adjusting the pH of said aqueous solution to a pH of from about pH 4 to about pH 10, at a first temperature of at least about 70° C.; and cooling said solution to a second temperature of less than about 70° C.

21. The process as defined in claim 20 wherein said trovafloxacin acid addition salt is trovafloxacin mesylate, said pH is about pH 7, said first temperature is about 70° C.; and said second temperature is RT.

22. A pharmaceutical composition comprising the crystal as defined in claim 1, and a pharmaceutically acceptable vehicle, diluent or carrier.

23. A pharmaceutical composition for oral administration as defined in claim 22.

24. A suspension as defined in claim 23, provided that, said suspension comprises an amount of water sufficient to maintain said six-sided lath form.

25. A pharmaceutical composition comprising the crystal as defined in claim 2, and a pharmaceutically acceptable vehicle, diluent or carrier.

26. A pharmaceutical composition for oral administration as defined in claim 25.

27. A suspension as defined in claim 26, provided that, said suspension comprises an amount of water sufficient to maintain said four-sided lath form.

28. A pharmaceutical composition comprising the crystal as defined in claim 3, and a pharmaceutically acceptable vehicle, diluent or carrier.

29. A pharmaceutical composition for oral administration as defined in claim 28.

30. A suspension as defined in claim 29.

31. A method of treating a bacterial infection in a mammal which comprises administering to said mammal an effective treating amount of a crystal as defined in claim 1.

32. The method as defined in claim 31 wherein said mammal is a human being.

33. A method of treating a bacterial infection in a mammal which comprises administering to said mammal an effective treating amount of a crystal as defined in claim 2.

34. The method as defined in claim 33 wherein said mammal is a human being.

35. A method of treating a bacterial infection in a mammal which comprises administering to said mammal an effective treating amount of a crystal as defined in claim 3.

36. The method as defined in claim 35 wherein said mammal is a human being.

37. The suspension as defined in claim 24 wherein the pH is from about pH 6 to about pH 8.

38. The suspension as defined in claim 37 wherein the amount of said crystal is from about 1 mg/mL to about 40 mg/mL.

39. The suspension as defined in claim 37 further comprising a suspending agent, an anti-caking agent, one or more preservatives, and one or more buffering agents.

40. The suspension as defined in claim 39 further comprising a sweetening agent.

41. The suspension agent as defined in claim 40 further comprising a flavoring agent.

42. The suspension as defined in claim 41 wherein said suspending agent is xanthan gum, said anti-caking agent is colloidal silicon dioxide, said preservatives consist of methyl paraben, propyl paraben, and butyl paraben, said buffering agents consist of sodium phosphate dibasic anhydrous and sodium phosphate monobasic monohydrate, said sweetening agent is sucrose, and said flavoring agent is strawberry flavoring.

43. The suspension as defined in claim 42 wherein the amount of said crystal is from about 1 mg/mL to about 40 mg/mL, the amount of said xanthan gum is from about 0.05 weight % to about 1.0 weight %, the amount of said colloidal silicon dioxide is from about 0.01 weight % to about 2.0 weight %, the amount of said methyl paraben is from about 0.5 mg/mL to about 3.0 mg/mL, the amount of said propyl paraben is from about 0.05 mg/mL to about 0.3 mg/mL, the amount of said butyl paraben is from about 0.05 mg/mL to about 0.2 mg/mL, the amount of each of said sodium phosphate dibasic anhydrous and said sodium phosphate monobasic monohydrate is from about 5 mM to about 100 mM, the amount of said sucrose is from about 10 weight % to about 60 weight %, and the amount of said strawberry flavoring is from about 0.01 weight % to about 1.0 weight %, where weight % is based on the total weight of said suspension.

44. The suspension as defined in claim 43 wherein said amount of said crystal is from about 10 mg/mL to about 30 mg/mL, said amount of said xanthan gum is from about 0.20 weight % to about 0.30 weight %, said amount of said colloidal silicon dioxide is from about 0.05 weight % to about 0.20 weight %, said amount of each of said sodium phosphate dibasic anhydrous and said sodium phosphate monobasic monohydrate is from about 10 mM to about 30 mM, said amount of said sucrose is from about 10 weight % to about 30 weight %, and said amount of said strawberry flavoring is from about 0.30 weight % to about 0.60 weight %.

45. The suspension as defined in claim 44 wherein said amount of said crystal is about 10 mg/mL, said amount of said xanthan gum is about 0.25 weight %, said amount of said colloidal silicon dioxide is about 0.10 weight %, said amount of said methyl paraben is about 1.0 mg/mL, said amount of said propyl paraben is about 0.2 mg/mL, said amount of said butyl paraben is about 0.10 mg/mL, said amount of each of said sodium phosphate dibasic anhydrous and said sodium phosphate monobasic monohydrate is about 30 mM, said amount of said sucrose is about 20 weight %, and said amount of said strawberry flavoring is about 0.60 weight %.

46. An aqueous suspension comprising a crystal as defined in claim 1 and an amount of water sufficient to maintain said six-sided lath form.

47. An aqueous suspension comprising a crystal as defined in claim 2 and an amount of water sufficient to maintain said four-sided lath form.

* * * * *